United States Patent [19]

Liboff et al.

[11] Patent Number: 5,160,591
[45] Date of Patent: * Nov. 3, 1992

[54] METHODS AND APPARATUS FOR REGULATING TRANSMEMBRANE ION MOVEMENT UTILIZING SELECTIVE HARMONIC FREQUENCIES AND SIMULTANEOUS MULTIPLE ION REGULATION

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[*] Notice: The portion of the term of this patent subsequent to Jun. 12, 2007 has been disclaimed.

[21] Appl. No.: 764,666

[22] Filed: Oct. 25, 1991

Related U.S. Application Data

[63] Continuation of Ser. No. 343,017, Apr. 25, 1989, Pat. No. 5,073,238, which is a continuation-in-part of Ser. No. 280,848, Dec. 7, 1988, Ser. No. 172,268, Mar. 23, 1988, Pat. No. 4,932,951, Ser. No. 265,265, Oct. 31, 1988, Pat. No. 5,067,940, Ser. No. 254,438, Oct. 6, 1988, Pat. No. 5,106,361, and Ser. No. 295,164, Jan. 9, 1989, Pat. No. 5,100,373, said Ser. No. 280,848, is a continuation of Ser. No. 923,760, Oct. 27, 1988, Pat. No. 4,818,697.

[51] Int. Cl.$^5$ .................................................. A61N 2/04
[52] U.S. Cl. ................................. 204/155; 600/13; 600/15; 128/419 F
[58] Field of Search ............... 204/155; 600/13, 15; 128/419 F

[56] References Cited

U.S. PATENT DOCUMENTS

| | | | |
|---|---|---|---|
| 3,566,377 | 3/1971 | Smith et al. | 128/422 |
| 3,890,953 | 6/1973 | Kraus et al. | 128/1.5 |
| 3,893,462 | 7/1975 | Manning | 128/421 |
| 3,911,930 | 10/1975 | Hagfors et al. | 128/421 |
| 3,952,751 | 4/1976 | Yarger | 128/422 |
| 4,105,017 | 8/1978 | Ryaby et al. | 128/1.5 |
| 4,266,532 | 5/1981 | Ryaby et al. | 128/1.5 |
| 4,428,366 | 1/1984 | Findl et al. | 128/15 |
| 4,459,988 | 7/1984 | Dugot | 128/419 |
| 4,535,775 | 8/1985 | Brighton et al. | 128/419 |
| 4,548,208 | 10/1985 | Niemi | 128/419 |
| 4,561,426 | 12/1985 | Stewart | 128/1.5 |
| 4,600,010 | 7/1986 | Dugot | 128/419 |
| 4,616,629 | 10/1986 | Moore | 128/1.5 |
| 4,622,952 | 11/1986 | Gordon | 128/1.3 |
| 4,622,953 | 11/1986 | Gordon | 128/1.3 |
| 4,654,574 | 3/1987 | Thaler | 320/14 |
| 4,683,873 | 8/1987 | Cadossi et al. | 128/1.5 |
| 4,757,804 | 7/1988 | Griffith et al. | 128/1.5 |
| 4,932,951 | 6/1990 | Liboff et al. | 606/13 |
| 5,067,940 | 11/1991 | Liboff et al. | 600/13 |

OTHER PUBLICATIONS

"Stimulation of Fracture Healing with Electromagnetic Fields of Extremely Low Frequency (EMF of ELF)"; Ola Wahlstrom, M.D.; Clinical Orthopaedics and Related Research, No. 186, Jun., 1984.

"Interactions Between Elecromagnetic Fields and Cells"; Chiabrera et al., (Plenum Publishing Corp., 1985).

(List continued on next page.)

Primary Examiner—John Niebling
Assistant Examiner—Arun S. Phasge
Attorney, Agent, or Firm—Dykema Gossett

[57] ABSTRACT

Methods and apparatus for regulating ion movement across biological membranes are provided. In one aspect, harmonic frequencies of a fluctuating magnetic field based on cyclotron resonance principles are provided for selectively enhancing transmembrane ion movement. In another aspect, a method and apparatus are provided for simultaneously regulating the transmembrane movement of multiple distinct ionic species using a fluctuating magnetic field. Therapeutic applications of harmonic tuning and multiple tuning are also provided.

1 Claim, 3 Drawing Sheets

OTHER PUBLICATIONS

"A Role for the Magnetic Field in the Radiation-Induced Efflux of Calcium Ions From Brain Tissue in Vitro", Blackman et al.; Bioelectromagnetics 6:327-337 (1985).

"Bioelectrochemical Studies of Implantable Bone Stimulation Electrodes"; Bioelectrochemistry and Bioenergetics 5, 232-238 (1978).

"Inducing Bone Growth in Vivo by Pulse Stimulation", Levy et al., Clinical Orthopaedics and Related Research; No. 82, Oct. 1972.

"Clinical Experiecnes with Low Intensity Direct Current Stimulation of Bone Growth"; Becker et al., Clinical Orthopaedics and Related Research; No. 124; May 1977.

"Geomagnetic Cyclogron Resonances in Living Cells"; Liboff; Journal of Biological Physics, vol. 13, 1985.

"Effects of ELF(1-120 Hz) and Modulated (50 Hz) RF Fields on the Efflux of Calcium Ions from Brain Tissue in Vitro"; Blackman et al.; Bioelectromagnetics 6:1-11 (1985).

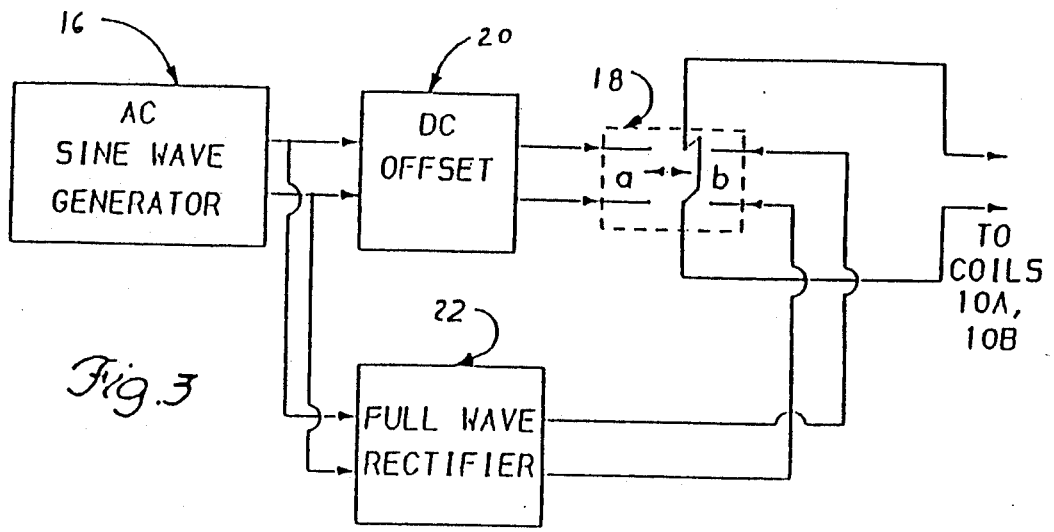
Fig. 3
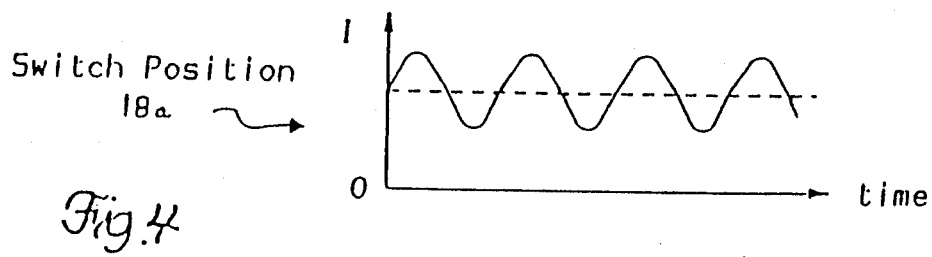
Fig. 4
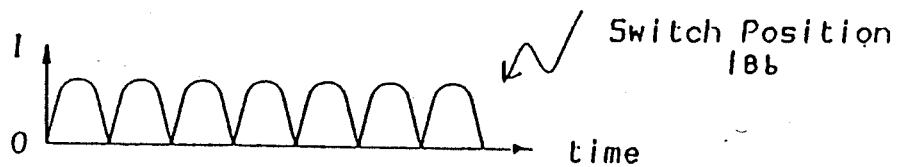
Fig. 5
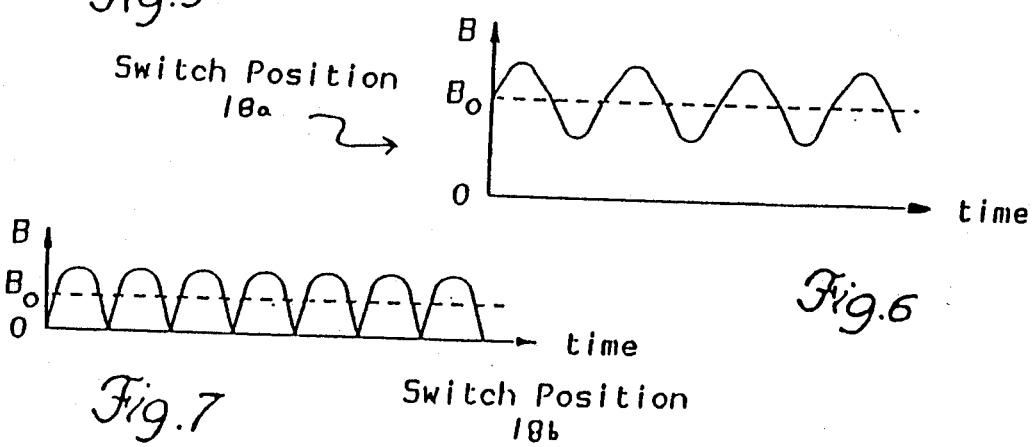
Fig. 6
Fig. 7

METHODS AND APPARATUS FOR REGULATING TRANSMEMBRANE ION MOVEMENT UTILIZING SELECTIVE HARMONIC FREQUENCIES AND SIMULTANEOUS MULTIPLE ION REGULATION

This is a continuation of copending application(s) Ser. No. 07/343,017 filed on Apr. 25, 1989, now U.S. Pat. No. 5,073,238, which is a continuation-in-part of each of the following United States Patent applications, the disclosures of which are all expressly incorporated herein by reference: U.S. patent application Ser. No. 07/280,848, filed Dec. 7, 1988; U.S. patent application Ser. No. 07/172,268, filed Mar. 23, 1988, now U.S. Pat. No. 4,932,951; U.S. patent application Ser. No. 07/265,265, filed Oct. 31, 1988, now U.S. Pat. No. 5,067,940; U.S. patent application Ser. No. 07/254,438, filed Oct. 6, 1988, now U.S. Pat. No. 5,106,361; and U.S. patent application Ser. No. 07/295,164, filed Jan. 9, 1989, now U.S. Pat. No. 5,100,373. Ser. No. 280,848 is in turn a continuation of Ser. No. 06,923,760, filed Oct. 27, 1988, now U.S. Pat. No. 4,818,697.

FIELD OF THE INVENTION

The present invention relates generally to methods and apparatus for regulating the movement of ions across cell membranes. More specifically, the present invention provides methods and apparatus for regulating the transmembrane movement of preselected ions in biological systems using selected harmonic frequencies which are based on the charge-to-mass ratio of the preselected ions. The present invention also provides a method and apparatus for simultaneously regulating the transmembrane movement of two or more distinct ionic species across a membrane. The present invention further provides methods and apparatus for the therapeutic treatment of selected body tissues.

BACKGROUND OF THE INVENTION

The role of biological ions as mediators of cellular activity is well established. In U.S. patent application Ser. No. 923,760, now U.S. Pat. No. 4,818,697, the inventors of the present invention disclose novel techniques for controlling the movement of a preselected ionic species across the membrane of a living cell. Therein, the relationship between ion movement and fluctuating magnetic fields is described and a method and apparatus are provided by which ion movement can be selectively controlled. Having discovered that ion movement through a biochemical membrane can be controlled by creating a specific relationship between the strength of a fluctuating magnetic field and the rate of the field oscillation, and that the relationship can be predicted using the cyclotron resonance equation, the frequency of which is:

$$f_c = \frac{Bq}{2\pi m}$$

the present inventors provided a foundation on which a number of useful inventions are based.

Accordingly, in U.S. patent application Ser. No. 923,760, it is disclosed that by exposing a region of living tissue of a subject such as a human or animal subject to an oscillating magnetic field of predetermined flux density and frequency, the rate of tissue growth can be controlled. Specifically, it is disclosed therein that by tuning a fluctuating magnetic field to the specific cyclotron resonance frequency of a preselected ion such as Ca++ or Mg++, the rate of bone growth can be stimulated. It is anticipated that this treatment will be highly beneficial in the treatment of fractures, bone non-unions, and delayed unions. In addition, the use of cyclotron resonance tuning to control the growth rate of non-osseous, non-cartilaginous connective solid tissue is described in U.S. patent application Ser. No. 254,438, now U.S. Pat. No. 5,106,361. In U.S. patent application Ser. No. 265,265, now U.S. Pat. No. 5,067,940, a method and apparatus based on cyclotron resonance tuning are disclosed which allow the growth rate of cartilaginous tissue to be regulated. Still another important use of cyclotron resonance tuning, one of particular significance in the treatment of elderly patients, is disclosed in U.S. patent application Ser. No. 295,164. Therein, a method and apparatus for treating and preventing osteoporosis, both locally and systemically, is set forth. Therefore, it will be appreciated that cyclotron resonance regulation of ion movement is instrumental in a number of highly beneficial inventions in the field of medicine.

As described more fully in the foregoing United States patent applications, the inventors of the present invention discovered that ion movement through cell membranes can be achieved with the use of a magnetic field generating device in connection with an oscillator for creating a fluctuating magnetic flux density where a predetermined relationship between frequency and field strength is established. Preferably the magnetic field generating device includes a pair of Helmholtz coils. A cell or region of tissue, such as bone, cartilage or the like, is positioned between the Helmholtz coils such that a uniform magnetic field of controlled parameters permeates the target cell or tissue. As will be appreciated, in most instances the cell or tissue which is exposed to the applied magnetic field is also subject to a local magnetic field having a component in the direction of the applied field. In these applications, a magnetic field sensing device is provided to measure the combined or total magnetic flux, i.e. the sum of the applied magnetic field parallel to an axis which extends through the cell and the component of the local field in this direction.

In the preferred embodiments of the foregoing inventions, the charge-to-mass ratio of an ion, the transmembrane movement of which is to be regulated, is used to determine the frequency at which the applied magnetic field is oscillated to provide a predetermined relationship between the charge-to-mass ratio of the ion and the strength and frequency of the magnetic field. This relationship is determined using the cyclotron resonance equation, $f_c = Bq/2\pi m$, where $f_c$ is the frequency of the oscillating magnetic field in Hertz, q/m is the charge-to-mass ratio of the ion in Coulombs per kilograms, and B is a non-zero average value of the magnetic flux density in Tesla along the axis permeating the subject cell or tissue. When the field includes a component of the local filed, this value is a non-zero net average value of the combined or resultant magnetic field.

The present invention is directed toward certain modifications in cyclotron resonance regulation of ion movement. More specifically, the present invention addresses the desirable goal of simultaneously regulating transmembrane movement of two different ionic species, for example Ca++ and Mg++, and also to additional frequencies which are effective for a single ion.

Therefore, it is an object of the present invention to provide a method and apparatus by which the movement of a single ionic species across a cell membrane can be regulated by a fluctuating magnetic field having a frequency selected from a group of frequencies based on the fundamental cyclotron resonance frequency. It is a further object of the present invention to provide a method and apparatus by which the transmembrane movement of two or more distinct ionic species in a single system may be simultaneously regulated using a fluctuating magnetic field having a predetermined ratio between the frequency and average field strength. It is still a further object of the present invention to provide a number of techniques for the therapeutic treatment of biological subjects which are based on the tuning principles set forth herein.

SUMMARY OF THE INVENTION

In accordance with the present invention there is provided in one aspect a method for regulating the movement of a preselected ion across a cell membrane. The method includes the steps of generating an applied magnetic field parallel to a predetermined axis which projects through a space in which at least one living cell or a target tissue is positioned. The cell or target tissue is surrounded by a fluid in the presence of a preselected ion. The applied magnetic field, alone or in combination with a component of the local magnetic field parallel to the predetermined axis, permeates the target cell or tissue. The applied magnetic field is fluctuated at a predetermined rate such that the magnetic flux density along the predetermined axis, which in the presence of a local magnetic field includes the local component, has a non-zero average value.

Transmembrane movement of a preselected ion is controlled by creating and maintaining a predetermined relationship between the frequency of the fluctuations and the non-zero average value of the magnetic flux density along the predetermined axis based on the charge-to-mass ratio of the preselected ion. This predetermined relationship is determined using the equation $f_{ch}=XBq/2\pi m$ where $f_{ch}$ is the frequency of the fluctuating magnetic flux density in Hertz, B is the non-zero average value of the flux density parallel to the predetermined axis in Tesla, q is the charge of the preselected ion in Coulombs, m is the mass of the preselected ion in kilograms, and X is a preselected odd integer greater than one. In this manner, a number of higher harmonic frequencies are provided by which transmembrane movement of a preselected ionic species can be regulated. An inventive apparatus for carrying out the method of the present invention is also provided.

In another aspect, the present invention provides a method for simultaneously regulating the transmembrane movement of two or more different ions across a cell membrane. In a preferred embodiment, the method comprises generating an applied magnetic field parallel to a predetermined axis which projects through a designated space. In the presence of at least two different predetermined ionic species, a living cell or tissue in a biological fluid is placed in the designated space such that the target cell or tissue is exposed to the applied magnetic field. In one embodiment, the target cell or tissue is also exposed to a local magnetic field having a component parallel to the predetermined axis. The magnetic flux density along the predetermined axis is fluctuated to create a non-zero average value. Where a local field is also present, this non-zero average value is the net non-zero average value of the applied and local field components parallel to the predetermined axis.

A predetermined relationship between the frequency of the fluctuations and the non-zero average value of the magnetic flux density along the axis is then created and maintained which simultaneously controls the movement of two or more preselected ions. In one embodiment, the predetermined relationship is determined by first solving the equation $f_c=Bq/2\pi m$ at a generally randomly selected value of B for each distinct preselected ion, where $f_c$ is the frequency of the field fluctuations in Hertz, B is the non-zero average value of the flux density parallel to the predetermined axis in Tesla, q is the charge of each preselected ion in Coulombs, and m is the mass of each preselected ion in kilograms. The value of b is preferably between about 1.0 and about 10,000 $\mu$ Tesla. This establishes the fundamental cyclotron frequency for each ion. A value $f_{cs}$, not necessarily equal to $f_c$, is then determined at which the magnetic flux density is oscillated. The value of $f_{cs}$ is preferably selected such that none of the individual ion $f_c$ values deviate more than 5 percent from the $f_{cs}$ value. In most instances, there will be no $f_{cs}$ value available based on the fundamental $f_c$ values of the preselected ions. Accordingly, a higher odd harmonic frequency of at least one of the preselected ions is determined with the equation $f_{ch}=XBq/2\pi m$ as previously explained. The values of $f_c$ and $f_{ch}$ are examined to determine whether an $f_{ch}$ value can be selected based on a 10 percent and most preferably a 5 percent deviation factor. If not, the process is continued for each value of $f_{ch}$, beginning with the lowest odd harmonic $f_{ch}$ values until a value of $f_{cs}$ can be established within the 5 percent deviation. Hence, at the value selected for B during the calculation of the $f_c$ or $f_{ch}$ values, the magnetic flux density to which the target cell or tissues exposed is fluctuated along the axis at the $f_{cs}$ frequency. This specific relationship between frequency and field strength brings about simultaneous transmembrane movement of the preselected ions. An apparatus adapted to simultaneously regulate more than one ionic species in this manner is also provided.

In still another aspect of the present invention, the concepts of harmonic tuning and multiple ion tuning are used for therapeutic treatment of a region of tissue in a human or animal subject. In particular, the present invention provides a therapeutic treatment modality for bone tissue to stimulate bone growth and/or reduce osteoporosis. In still another embodiment, the growth characteristics of cartilaginous tissue or non-osseous, non-cartilaginous connective tissue are regulated. In still another aspect, systemic treatment and/or prevention of osteoporosis is also provided.

BRIEF DESCRIPTION OF THE DRAWINGS

These and other advantages and features of the invention will be described more fully hereinafter and in connection with the accompanying drawings in which:

FIG. 3 is a schematic electrical diagram of an apparatus for generating the ion-regulating, fluctuating magnetic field of the present invention.

FIGS. 4 through 7 illustrate signal waveshapes generated by the apparatus shown in FIG. 3.

DESCRIPTION OF THE PREFERRED EMBODIMENTS

Figure 1:
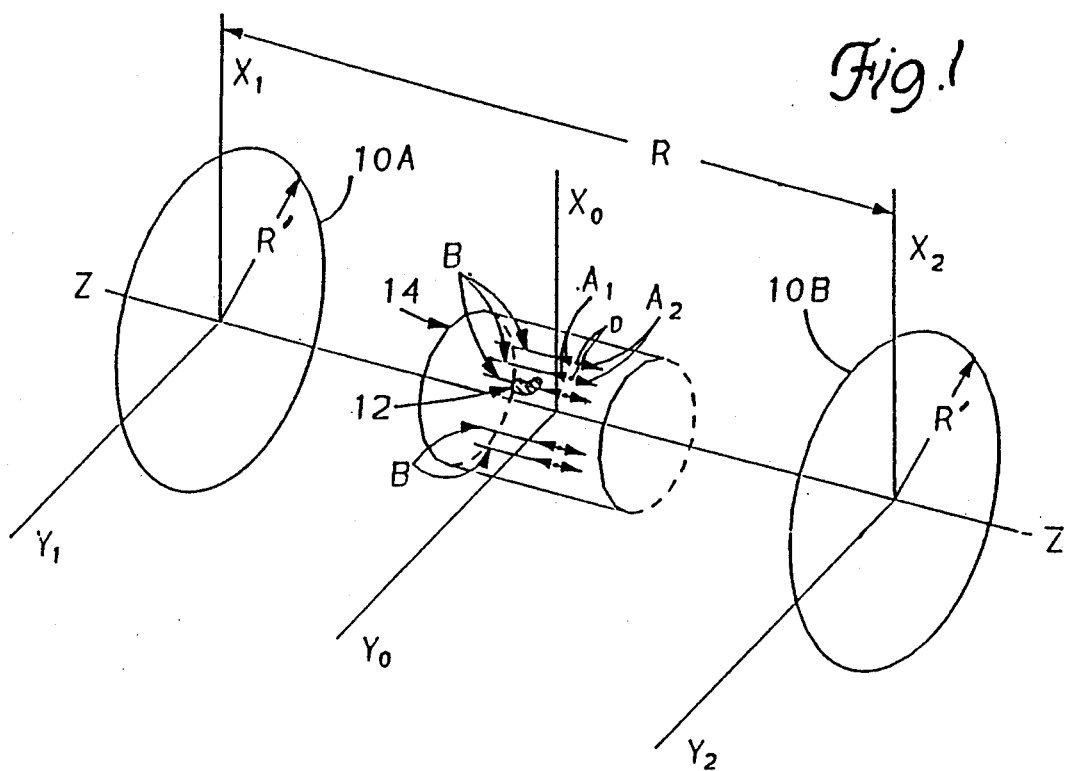
FIG. 1 is a schematic, perspective view of a living cell exposed to a fluctuating magnetic field in accordance with the present invention.

Referring now to FIG. 1 of the drawings, a pair of field coils 10A and 10B having the arrangement and attributes set forth more fully in the aforementioned U.S. patent application Ser. No. 923,760 are seen by which an applied magnetic field is generated which permeates living cell 12 in predetermined volume or space 14. As will become more apparent hereinafter, living cell 12 may comprise one or more distinct cells, cell aggregates, organoids or tissue. In particular, living cell 12 may comprise a region of tissue such as a region of bone in a living host, either man or animal. Cell 12 contains a specific complement of intracellular ionic species and will generally be surrounded by a liquid containing ionic species required for cell and tissue function.

Coils 10A and 10B, as well as space 14 are shown in relation to a rectangular coordinate axis system with the mid-planes of each coil positioned at $X_1$, $Y_1$, and $X_2$, $Y_2$ and separated by a distance R. The center of each coil is aligned with the Z-axis and has a radium $R'$. Those skilled in the art will recognize that coils 10A and 10B are arranged in Helmholtz configuration. Accordingly, a uniform applied magnetic field having a flux density B is generated in space 14 by coils 10A and 10B. As will be explained more fully, in most applications, B will be the average value of the net or combined magnetic flux density in space 14 resulting from the applied field and a pre-existing local field component such as the earth's geomagnetic field. Thus, a magnetic field of known, controllable parameters permeates cell 12 along a predetermined axis. The value of B may be preferably measured by a magnetic field sensor or the like. In the present invention, the applied magnetic field is fluctuated at a predetermined frequency. This characteristic is illustrated by opposed arrows A1 and A2 which are separated by a dot "D."

Figure 2:
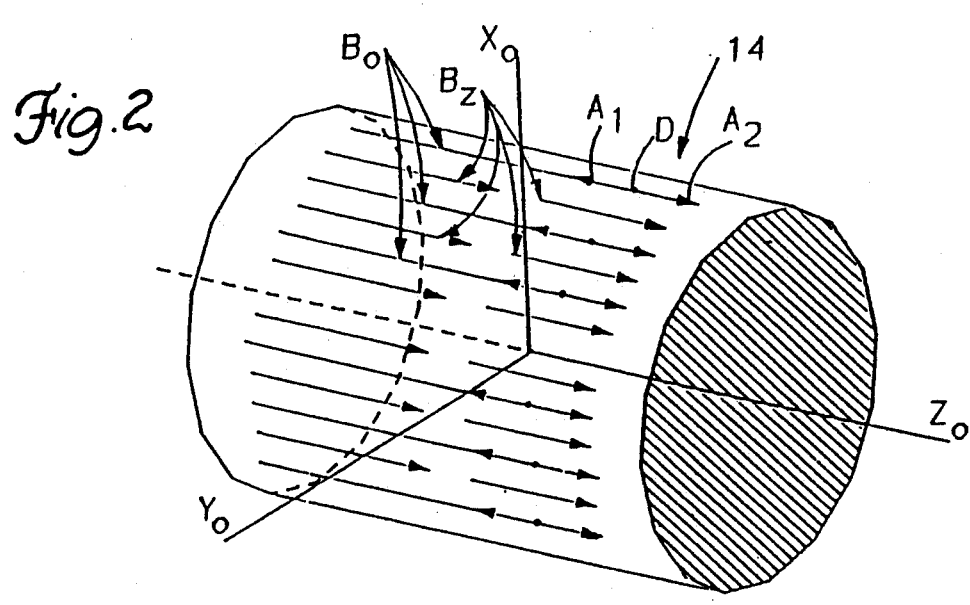
FIG. 2 is a schematic diagram illustrating the formation of a combined or net magnetic flux density which includes a local field component in accordance with the present invention.

Referring now to FIG. 2 of the drawings, in that embodiment of the present invention in which space 14 is subject to a local magnetic field, the local magnetic field will have a component vector in the direction of the Z-axis which penetrates space 14 and cell 12. The Z-axis represents the aforementioned predetermined axis which extends through the target cell or tissue to be influenced in accordance with the present invention. It is that component of the magnetic field parallel to this predetermined axis which is regulated to produce transmembrane ion movement in the present invention. In FIG. 2, the applied magnetic field which is parallel to the predetermined axis Z is shown as $B_o$. The local magnetic field component parallel to the Z-axis is illustrated as $B_z$. It is to be understood that space 14 represents the region in which the magnetic flux density as regulated by the present invention is substantially uniform. Space 14 should be large enough to accommodate the target cell or tissue to be treated. In this embodiment, B is the average value of the combined applied and local field components, i.e. the net average value of the sum of $B_O$ and $B_Z$.

Referring now to FIG. 3 of the drawings, in one embodiment coils 10A and 10B receive electrical signals from a conventional AC sine wave generator 16 connected by means of a switch 18 either to a DC offsetting network 20 or a full-wave rectifier 22, although other waveforms may be suitable. The instantaneous current I supplied to coils 10A and 10B as a function of time is shown for both switch positions 18A and 18B in FIGS. 4 and 5, respectively. Similarly, the instantaneous magnetic flux density, $B_o$ in FIG. 2, produced within space 14 is depicted as a function of time for both switch positions 18A and 18B in FIGS. 6 and 7, respectively.

When coils 10A and 10B are energized by the apparatus shown in FIG. 3 of the drawings, the coils generate a magnetic flux density within volume 14 that varies with time as shown in FIGS. 6 and 7. An applied non-zero average magnetic flux density B, uniform throughout space 14, results either from an offset sinusoidal signal or from a full-wave rectified signal applied to coils 10A and 10B. As stated, where space 14 is subject to a local magnetic field, B is the net non-zero average magnetic flux density of the applied and local field parallel to the predetermined axis. The effect of this Z-component of the local flux density will be to change the non-zero average applied magnetic flux density $B_o$ shown in FIG. 2 a different net average value.

As fully explained in the aforementioned U.S. patent application Ser. No. 923,760, by creating a relationship between the rate of fluctuation or frequency of the magnetic field parallel to the predetermined axis which extends through space 14 and thus through the target tissue or cell 12, and the magnetic flux density along this axis, a fundamental frequency based on the charge-to-mass ratio of a preselected ionic species can be determined at which movement of the preselected ionic species across the cell membrane can be regulated. The parameters of this relationship are determined with reference to the cyclotron resonance frequency $f_c = Bq/2\pi m$. In other words, the magnetic flux density along the Z-axis, which includes a local component vector if a local field exists, is regulated such that the charge-to-mass ratio of the preselected ion equals the ratio of $2\pi$ times the supplied frequency $f_c$ times the non-zero average magnetic flux density B.

In the present invention, this fundamental frequency, $f_c$, is effectively multiplied by a selected odd integer to produce a frequency which also causes the preselected ion to move across the cell membrane of cell 12. Unless otherwise specified, as used herein, the term "odd integers" or "odd integer" shall mean positive, non-zero integers. The preferred odd integers for use in the present invention which provide harmonic frequencies that are effective in causing transmembrane ion movement are selected from the group consisting of the following integers: three, five, seven, nine, eleven, thirteen, fifteen, seventeen and nineteen. Additional harmonic frequencies based on multiplying the fundamental frequency by an odd integer may also be suitable in some applications. Even integers have not been found useful. The frequencies for a given preselected ion and known magnetic flux density B can be determined with reference to the equation $f_{ch} = XBq/2\pi m$ where $f_{ch}$ is the frequency in Hertz of the fluctuating magnetic field along a predetermined axis extending through the target tissue, B is the magnetic flux density along the axis in Tesla, q is the charge of the preselected ion in Coulombs, m is the mass of the preselected ion in kilograms, and X is a selected odd integer greater than one. It has been found that many of the preferred odd multiple harmonic frequencies are substantially as effective in promoting transmembrane ion movement as are the fundamental frequencies. As stated, the preferred values of X are the odd integers three, five, seven, nine, eleven, thirteen, fifteen, seventeen, and nineteen. Ion movement of a number of ionic species can be controlled or regulated in this manner, including $Ca^{++}$, $Mg^{++}$, $K^+$, $Li^+$, $Na^+$, $Cl^+$ and $HCO_3^+$. Other ions may be also suitable in a particular application.

In those applications where random changes in the local field component along the predetermined axis may occur, it is preferred that the magnetic field generating device of the present invention include a magnetic field sensor, such as a Hall effect device, to measure the magnetic flux density B along the predetermined axis. It is also preferred that microprocessing means described in the aforementioned U.S. patent application Ser. No. 172,268 be included with the field generator and magnetic sensor such that the rate of fluctuation ($f_{ch}$) of the field and/or the value B of the field can be automatically changed to compensate for changes in the local field component. This allows the predetermined relationship to be maintained despite these local changes.

In the preferred embodiment of the present invention, the concept of tuning the cyclotron resonance frequency to an odd harmonic as previously described is used in connection with the therapeutic treatment modalities as described in the aforementioned U.S. patent applications Ser. Nos. 172,268, 265,265, 254,438 and 295,164. More specifically, and referring now to FIG. 8 of the drawings, treatment apparatus 30 is shown having treatment heads 32 and 34, each of which encloses a field coil such that treatment heads 32 and 34 comprise a pair of Helmholtz coils by which a uniform magnetic field is generated in space 36, which in this instance is occupied by a region of living tissue. The general design of treatment apparatus 30 is explained in more detail in U.S. patent application Ser. No. 172,268, which is incorporated herein by reference. Accordingly, and for the purposes of illustration, a human femur 38 having fractured ends 40 and 42 is shown in phantom within leg 44. In order to stimulate the growth of fractured ends 40 and 42, a fluctuating magnetic field is established using treatment apparatus 30 in which the frequency of fluctuations is determined with reference to the aforementioned modification of the cyclotron resonance equation: $f_c = XBq/2\pi m$. In a preferred aspect, X is 3 and the preselected ionic species is calcium. Magnesium and potassium regulation, in addition to other ions, is also useful. Accordingly, in one preferred embodiment, a frequency of 15.31 hertz is established for the $Ca^{++}$ ion where the combined or composite magnetic flux density parallel to a predetermined axis A has a net non-zero average value of 20.0 μ Tesla and a peak-to-peak amplitude of 40.0 μ Tesla to stimulate bone growth. The higher harmonic tuning of the present invention is similarly useful in the regulation of cartilage growth and the growth of non-osseous, non-cartilaginous connective tissue as described in the aforementioned U.S. patent applications. For stimulating cartilage growth a frequency of 75.71 Hertz at a B value of 20.0 μ Tesla with a peak-to-peak amplitude of 40.0 μ Tesla is suitable. This represents cyclotron resonance tuning for the $Mg^{++}$ ion where X is 3. In the case of non-cartilaginous, non-osseous solid connective tissue a frequency of 15.31 Hertz with a B value of 20.0 μ Tesla and peak-to-peak amplitude of 40.0 μ Tesla is suitable for stimulating growth. This represents cyclotron resonance tuning to the $Ca^{++}$ ion where X is 1.

The present invention is also useful in the systemic treatment and/or prevention of osteoporosis as will now be described in connection with FIG. 9 of the drawings. Accordingly, systemic treatment apparatus 50 is shown which comprises a tube or cylinder 52 of a non-magnetic material such as plastic. Tube 52 houses a large solenoid 54 which contains multiple turns of wire 56 which extend substantially the entire length of systemic treatment apparatus 50. A gurney or platform 58 is provided on a track system (not shown) which allows platform 58 to move between a first position outside tube 52 to a second position inside tube 52. A controller 600 is provided along with the necessary circuitry for energizing solenoid 54 to create a magnetic field in the direction of axis 62, which in this embodiment projects through the central bore of solenoid 54 and subject 59. A fluctuating, and in most instances a combined or composite magnetic field, having a magnetic flux density parallel to predetermined axis 62 is generated. The combined magnetic flux density along the axis is maintained at a predetermined relationship to the frequency of the fluctuations. Again, the frequency of the fluctuating field is determined with reference to the equation $f_c = XBq/2\pi m$, where X is a selected odd integer. In the most preferred embodiment, the preselected ionic species to which the fluctuating magnetic field is tuned using this odd harmonic technique comprises $Ca^{++}$ where X is 5. This treatment is effective in diminishing or preventing osteoporosis in a human or animal subject.

In still another aspect of the preset invention, a method and apparatus for simultaneously regulating the transmembrane movement of two different ionic species is provided. This technique is based in part on the principles of odd harmonic frequencies as described above. In the development of cyclotron resonance tuning, the present inventors recognized that it may be desirable in some instances to simultaneously regulate the transmembrane movement of two or more preselected ions. In this manner, the benefits of ion movement of each such ion could be achieved simultaneously, and quite possibly, a beneficial synergism might be achieved. One such method of simultaneous multiple ion regulation is set forth in the aforementioned U.S. patent application Ser. No. 923,760. Therein, a method is disclosed for simultaneously enhancing the transmembrane movement of two distinctly different ionic species such as a hydrogen ion and a potassium ion. In the present invention, multiple ion tuning is achieved by regulating magnetic flux density along a single axis. In accordance with the present invention, a relationship between the frequency of the fluctuating magnetic field and a non-zero average value of the magnetic flux density is provided such that the field is simultaneously tuned to effect transmembrane movement of ore than one type of ionic species at the same time.

More specifically, it has been found that the fundamental cyclotron resonance frequency of a preselected ionic species may be within a few percent of a selected odd multiple of the fundamental frequency of a different ionic species. In addition, an odd harmonic cyclotron resonance frequency of one preselected ionic species may be substantially the same as a different odd harmonic frequency of another preselected ionic species. This principle of "harmonic overlap" may be extended to three, four, or possibly even a greater number of different ionic species where a "common" frequency can be found which is substantially equal to a fundamental or odd multiple harmonic frequency of each of the ionic species involved. In this manner, it is possible to simultaneously regulate the transmembrane movement of two or more different ionic species.

With reference now again to FIG. 1 of the drawings, the target tissue or cell 12 is placed between coils 10A and 10B in space 14, again in the presence of a liquid medium which may be the natural cell environment. At least two different ionic species to be regulated are present. A magnetic field having a flux density along a predetermined axis, the Z axis in FIG. 1, is generated in most embodiments a local magnetic field having a component along the predetermined axis will be present. A non-zero average value or net average value of the magnetic flux density to be initiated parallel to the axis is then selected. The value of B is preferably between about 1.0 to about 10,000 $\mu$ Tesla, with a peak-to-peak amplitude of about 2.0 to about 20,000 $\mu$ Tesla.

In one embodiment the fundamental frequency at which the fluctuating magnetic field would be oscillated for cyclotron resonance regulation of transmembrane ion movement is calculated individual for each different ionic species to be regulated using the equation $f_c = Bq/2\pi m$ for a selected value of B, which is again the non-zero average value of the flux density along the predetermined axis. As previously explained, $f_c$ as in Hertz, q as in Coulombs, and m is in kilograms. q/m is the charge-to-mass ratio of the preselected ion. Once the fundamental cyclotron resonance frequency ($f_c$) of each ion to be regulated is calculated, a regulating frequency ($f_{cs}$) is determined which is preferably within 5 percent of the fundamental frequency $f_c$ or an odd harmonic frequency $f_{ch}$ of each preselected ion. The odd harmonic frequencies are determined again using the equation $f_{ch} = XBq/2\pi m$, where X is an odd integer greater than one. It will be understood that the equation $f_{ch} = XBq/2\pi m$ can be used to determine the fundamental frequency, $f_c$, by using a value of 1 for X. While the value of $f_{cs}$ will not typically be available which is common to the fundamental frequencies and/or odd harmonic frequencies for each preselected ion, it has been found that an $f_{cs}$ value which is within about 10 percent and preferably about 5 percent of each fc value of $f_{ch}$ value of the ions to be regulated satisfactorily provides simultaneous transmembrane movement of each preselected ion in the field.

It will also be understood that the values of $f_{ch}$ are a function of B. Thus, it may be possible to obtain an $f_{cs}$ value for a particular set of ions which is within the preferred 5 percent deviation at a designated B value, but not a higher B value. For use in the present invention as applied to multiple simultaneous ion tuning, the value of B is preferably between about 1.0 to about 10,000 $\mu$ Tesla, with a peak-to-peak amplitude of about 2.0 to about 20,000 $\mu$ Tesla. Again, the waveform is not critical.

Accordingly, and referring now to FIG. 1 of the drawings, a magnetic flux density is generated with coils 10A and 10B along the Z axis which fluctuates at the multiple harmonic tuning value $f_{cs}$. The same considerations applicable in the previous embodiments with respect to the local component are also applicable to multiple ion tuning.

In order to fully illustrate this embodiment of the present invention, multiple ion tuning will be described in the case of two preferred ions, $Ca^{++}$ and $Mg^{++}$.

Referring to Table 1 below, the q/m ratios for $Ca^{++}$ and for $Mg^{++}$ are set forth along with the values of certain multiples of the q/m ratio, specifically 3, 5 and 15.

TABLE 1

| ION | q/m RATIO | X 3 | X 5 | X 15 |
|---|---|---|---|---|
| $Ca^{++}$ | 76.563 | 229.689 | 382.815 | 1148.445 |
| $Mg^{++}$ | 126.178 | 378.534 | 630.89 | 1892.67 |

It will be recognized that $f_{ch}$ is a function of the q/m ratio of each ion. For the $Mg^{++}$ ion 3 q/m is within 1.2% of the value of 5 q/m for the calcium ion. Thus, for a given value of B, for example, 20 microTesla, where X is 3 for $Mg^{++}$ and X is 5 for $Ca^{++}$, a range of values $f_{cs}$ can be determined which are within 5 percent of each $f_{ch}$ value. More specifically, in this example $f_{ch}$ for $Mg^{++}$ at 20 microTesla where X is 3 75.71 Hertz. Where X is 5, $f_{ch}$ for $Ca^{++}$ is 76.56 Hertz. It will be recognized that a number of values $f_{cs}$ can be selected which are within 5 percent of both $f_{ch}$ values. In one preferred embodiment, the mean value for the two $f_{ch}$ values is determined for use as the $f_{cs}$ value which in this example is 76.14 Hertz. An $f_{ch}$ value which deviates more than 5 percent from one or all of the $f_c$ or $f_{ch}$ values for the various ions may be suitable in some applications, although this 5 percent standard is preferred.

In another aspect, the multiple ion tuning of the present invention can be described in the case of harmonic overlap of two preselected ions in the following manner. A normalized cyclotron resonance frequency ($f_c/B_O$) is calculated using the equation:

$$\frac{f_c}{B_0} = \frac{Nq \; 10^{-4}}{2\pi m} \tag{I}$$

where $B_O$ is the magnetic flux density in Gauss along the axis, N is the valence charge number of the preselected ion (for example, N=2 for the $Ca^{++}$ ion and N=1 for the $Cl^-$ ion); q is $1.6 \times 10^{-19}$ Coulombs; and m is the ionic mass of the preselected ion in kilograms. Since it is known that $$m = \frac{(\text{atomic weight}) \; kg}{6.0253 \times 10^{26}} \tag{II}$$

then $$\frac{f_c}{B_0} = \frac{N(1534.33)}{\text{atomic weight of ion}} \tag{III}$$

By specifying a value for $B_O$, equation III above provides the fundamental cyclotron resonance frequency for the preselected ion. To then determine harmonic overlaps for two preselected ions, the following equation may be utilized:

$$\frac{(f_c/B_0)_j \; (H_j)}{(f_c/B_0)_k \; (H_k)} \approx 1$$

where $(f_c/B_O)_j$ is the normalized cyclotron resonance frequency for a preselected ion "j"; $(f_c/B_O)_k$ is the normalized cyclotron resonance frequency for a preselected ion "k"; $H_j$ is the harmonic number for ion "j"; and $H_k$ is the harmonic number for ion "k". The values of $H_j$ and $H_k$ may be any non-zero positive odd integer including 1.

To determine whether two preselected ions can be simultaneously regulated in accordance with the present invention, the following equation:

$$H_1 = \frac{(f_c/B_o)_k}{(f_c/B_o)_j} (H_2)$$

is utilized where the value of $H_2$ is any non-zero positive odd integer. In a preferred embodiment, $H_2$ is a positive odd integer from three to nineteen. Thus, a set of values for $H_1$ are defined.

The following table illustrates this method for several important biological ions:

| ION | N | AT. WT. | Fc/Bo | 3 | 5 | 7 | 9 | 11 | 13 | 15 | 17 | 19 |
|---|---|---|---|---|---|---|---|---|---|---|---|---|
| Cu | 1 | 63.54 | 24.147 | 72.44 | 120.74 | 169.03 | 217.33 | 265.62 | 313.92 | 362.21 | 410.51 | 458.80 |
| Ag | 2 | 108.87 | 28.448 | 85.34 | 142.24 | 199.13 | 256.03 | 312.93 | 369.82 | 426.72 | 483.61 | 540.51 |
| Gd | 3 | 157.25 | 29.272 | 87.82 | 146.36 | 204.90 | 263.45 | 321.99 | 380.53 | 439.08 | 497.62 | 556.16 |
| K | 1 | 39.102 | 39.239 | 117.72 | 196.20 | 274.67 | 353.15 | 431.63 | 510.11 | 588.59 | 667.07 | 745.54 |
| Cl | −1 | 35.453 | 43.278 | 129.83 | 216.39 | 302.35 | 389.50 | 476.06 | 562.61 | 649.17 | 735.72 | 822.28 |
| Zn | 2 | 65.37 | 46.943 | 140.83 | 234.71 | 328.60 | 422.49 | 516.37 | 610.26 | 704.14 | 798.03 | 891.92 |
| Co | 2 | 58.93 | 52.073 | 156.22 | 260.36 | 364.51 | 468.66 | 572.80 | 676.95 | 781.09 | 885.24 | 989.39 |
| Fe | 2 | 55.847 | 54.948 | 164.04 | 274.74 | 384.63 | 494.63 | 604.42 | 714.32 | 824.21 | 934.11 | 1044.00 |
| Mn | 2 | 54.94 | 55.855 | 167.56 | 279.27 | 390.98 | 502.69 | 614.40 | 726.11 | 837.82 | 949.53 | 1061.24 |
| Na | 1 | 22.99 | 66.739 | 200.22 | 333.70 | 467.17 | 600.65 | 734.13 | 867.61 | 1001.09 | 1134.56 | 1268.04 |
| Ca | 2 | 40.08 | 76.563 | 229.69 | 382.82 | 535.94 | 689.07 | 842.20 | 995.32 | 1148.45 | 1301.50 | 1454.70 |
| Mg | 2 | 24.32 | 126.178 | 378.54 | 630.89 | 883.25 | 1135.61 | 1387.96 | 1640.32 | 1892.68 | 2145.03 | 2397.39 |
| Li | 1 | 6.94 | 221.085 | 663.26 | 1105.43 | 1547.60 | 1989.77 | 2431.94 | 2874.11 | 3316.28 | 3758.45 | 4200.62 |

If two $H_2$ values exist which are positive odd integers or which have values close to that of positive odd integers, then a harmonic overlap exists at these values. To correspond with the aforementioned overlap range or band of frequencies which produce simultaneous ion movement of the two ionic species (i.e. preferably less than 5% deviation between the actual frequency ($f_{cs}$) and the $f_{ch}$ values), $H_1$ should not deviate more than 2.5% from an odd integer. To better illustrate this method, the technique will now be described with reference to $Ag^{++}$ and $Na^+$ at a $B_O$ of 0.2 Gauss.

Ion j = $Ag^{++}$  $(f_c/B_O)_j$ = 28.448

Ion k = $Na^{++}$  $(f_c/B_O)_k$ = 66.739

Therefore, $H_1 = 0.42625\ H_2$.

At $H_2$ values of 3, 5, 7, 9, 11, 13, 15, 17 and 19.

TABLE

| $H_1$ | $H_2$ |
|---|---|
| 0.42625 | (1) |
| 1.279 | (3) |
| 2.131 | (5) |
| 2.983 | (7) |
| 3.84 | (9) |
| 4.69 | (11) |
| 5.54 | (13) |
| 6.39 | (15) |
| 7.24 | (17) |
| 8.093 | (19) |

Based on these calculations, it is apparent that the value of $H_1$ where $H_2$ is 7 (i.e. 2.983), provides the necessary harmonic overlap conditions. Thus, $(f_c/B_O)Ag^{++}$ for the 7th harmonic ($H_2$=7) is 199.13

$(f_c/B_O)Na^+$ for the 3rd harmonic ($H_2$=3) is 200.22

Since $B_O$ = 0.2 Gauss = 20 μ Tesla,

7th $f_c Ag^{++}$ = 39.826 Hz

3rd $f_c Na^+$ = 40.04 Hz (This gives $\Delta F$ = 0.214 Hz)

It is important to also note that the overlap can be expanded by increasing the value of $B_O$. In the previous example, at 1000 μ Tesla, 7th $f_c Ag^{++}$ = 1991.13 Hz 3rd $f_c Na^+$ = 2002.2 Hz (This gives $\Delta f$ = 11.07 Hz)

Using this method for determining harmonic overlap for $Zn^{++}$ and $Ca^{++}$:

| $H_1 = .61313\ H_2$ | |
|---|---|
| $H_1$ | $H_2$ |
| 0.61313 | (1) |
| 1.839 | (3) |
| 3.066 | (5) |
| 4.29 | (7) |
| 5.52 | (9) |
| 6.74 | (11) |
| 7.97 | (13) |
| 9.197 | (15) |
| 10.42 | (17) |
| 11.65 | (19) |

It can be seen that the 5th harmonic of $Zn^{++}$ overlaps with the 3rd harmonic of $Ca^{++}$.

In its most preferred embodiment, fluctuations in the local field component which would otherwise alter the predetermined relationship provided by multiple ion tuning are counter-balanced by a microprocessor in association with the magnetic field generating means. Briefly, changes in the composite field due to changes in the local component are preferably measured by magnetic field sensor in association with the magnetic field generator. The microprocessor then adjusts the frequency of the field and/or the field strength to maintain the desired ratio of frequency-to-average magnetic flux density, which is always a non-zero average value. This technique is also suitable for counter-balancing changes in the local component in that embodiment of the present invention in which a single ionic species is regulated using a higher odd harmonic frequency. The microprocessor may also be programmed to automatically calculate $f_{cs}$ based on an input of the q/m ratios of the ions to be regulated.

Figure 8:
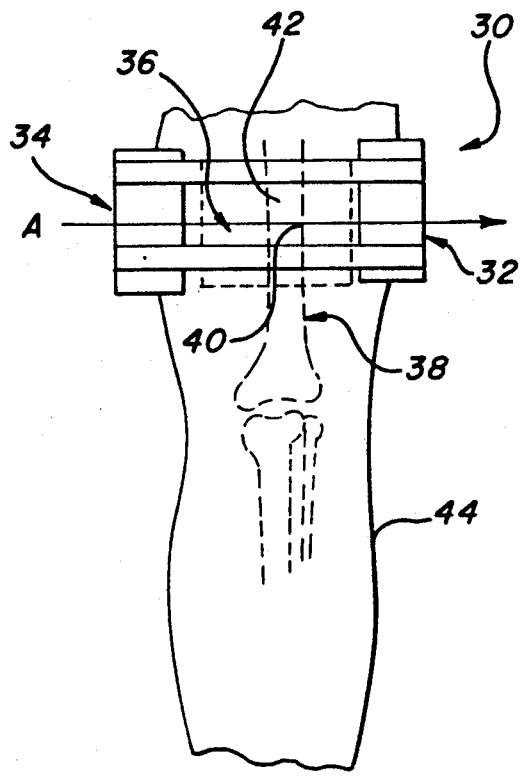
FIG. 8 illustrates the present invention for use in local treatment of living tissue in vivo.
Figure 9:
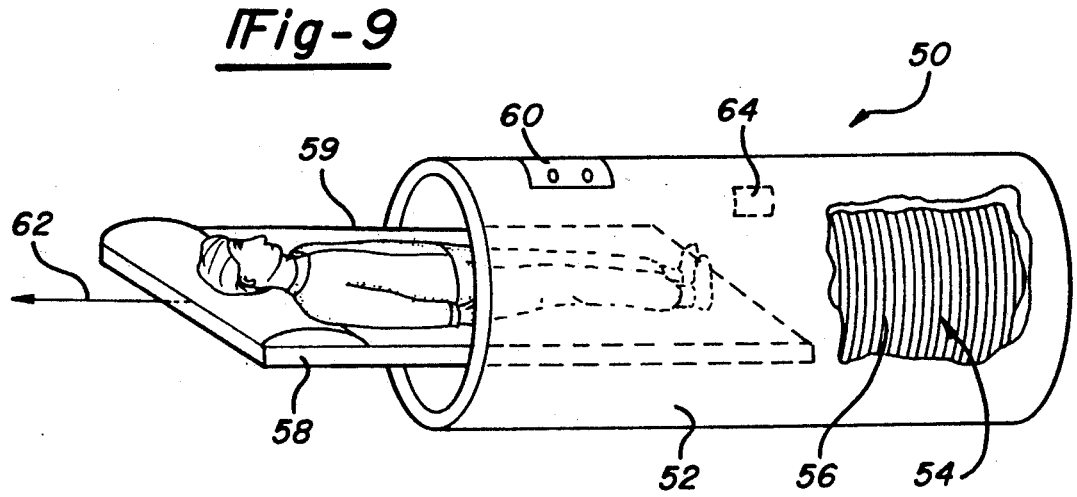
FIG. 9 illustrates the use of the present invention for providing systemic therapeutic treatment.

The present invention is particularly useful in controlling tissue growth using the apparatus shown in FIG. 8 of the drawings for effecting multiple ion tuning and in the treatment and prevention of osteoporosis in this manner and as shown in FIG. 9 of the drawings. More specifically, with respect to FIG. 8 of the drawings, treatment apparatus 30 is shown having treatment heads 32 and 34. Each treatment head contains a field coil such that treatment heads 32 and 34 comprise a pair of Helmholtz coils. To bring about a therapeutic treatment of a bone condition such as a fracture, non-union or delayed union, treatment heads 32 and 34 are positioned so that a uniform magnetic field can be generated in space 36, illustrated here as being occupied by fractured ends 40 and 42 of human femur 38. In order to accelerate the rate at which union of the fractured ends occurs, in this embodiment of the present invention, the frequency of the composite magnetic field is maintained at about 76 Hertz which is very close (within 5 percent) to the cyclotron resonance frequency of $Ca^{++}$ multiplied by a factor of 5 and $Mg^{++}$ multiplied by a factor of 3, where the non-zero net average value is 20 microTesla (peak-to-peak amplitude 40 μ Tesla). Changes in the local component which would otherwise change this relationship are counter-balanced by a magnetic field sensor (not shown) and a microprocessor (not shown) which sense changes in the local component and adjusts the field and/or applied magnetic flux to maintain this precise relationship. Treatment is continued until such time that beneficial results are attained, for example, from about one-half hour to six hours per day for approximately twelve weeks. Treatment within these parameters is effective in stimulating the growth of cartilaginous tissue, non-osseous non-cartilaginous tissue and solid connective tissue, as well as the local treatment or prevention of osteoporosis and the systemic treatment or prevention of osteoporosis utilizing the apparatus shown in FIG. 9.

The following examples are provided to more fully illustrate the present invention and are not intended to limit the scope of the invention as defined in the appended claims.

EXAMPLE 1

Diatoms were exposed to a fluctuating magnetic field in accordance with the present invention at both the fundamental frequency of 16 hertz for $Ca^{++}$ and then at odd multiples as provided by the equation $f_{ch}=XBq/2\pi m$ for $Ca^{++}$. It was noted than in addition to the fundamental frequency, where X was 3, 5 and 15, movement of diatoms (which is known to be brought about by increase in the intracellular concentration of calcium ions) was notably increased. Where X was 7, 9, 11, 13, and 17, increased motility was not produced.

EXAMPLE 2

Isolated in vitro 8-day chick femurs were exposed to a magnetic field harmonically "tuned" simultaneously for calcium and magnesium ions, according to the equation $f_{ch}=XBq/2\pi m$, where X=5 for $Ca^{++}$ and X=3 for $Mg^{++}$. At a non-zero net average value of B at 20.0 microTesla, which was the composite field as previously explained, $f_{cs}$ was set at 80 Hz. Increased bone growth was observed over controls.

In more detail, freshly-laid fertile white leghorn chicken eggs were obtained and which were incubated in a 100% humidified atmosphere at 40° C. for 8 days, and then removed and candled. For each run of the experiments, 26 eggs with normal-appearing embryos were selected. The eggs were opened, and the embryos removed to a sterile Petri dish. Any embryos abnormal in development or staging were discarded. The femurs of the embryos' legs were removed by blunt dissection with forceps and transferred in right-left pairs to sterile gauze squares moistened with Hanks' Balanced Salt Solution (HBSS) in another sterile dish. From this dish, paris were removed to squares of dry, sterile unbleached muslin, where they were rolled back and forth under a dissecting microscope until adhering tissue was removed, leaving bones stripped of all tissue except the perichondrium/periosteum. Tissue removal was confirmed microscopically. The right leg of each pair was reserved as a control, the left thus became an experimental subject.

The isolated femurs prepared for culture by the above method were placed into the wells of 12-well culture plates (Linbro). A small triangular type 316 stainless steel mesh screen was placed in each well. The corners had been folded under to lift the mesh slightly away from the bottom of the plate and allow for media circulation. A sterile triangle of thoroughly washed ordinary lens paper was placed atop the mesh screen, and the femurs were oriented in orthogonally positioned pairs on the lens paper. Thus, each femur could be identified later, since the wells were also numbered sequentially.

As each well was completed, it was given a 0.5 ml aliquot of sterile $BGJ_b$ medium (Fitton-Jackson modification, GIBCO) containing antibiotics and antimycotics (GIBCO). This amount was just sufficient to saturate the lens tissue and produce a meniscus of medium over the explanted femurs. It was noted that too much medium produced impaired growth, since gas exchange was also impaired if the femurs were beneath the surface of the medium. As soon as each plate was completed, it was covered and placed in either a control or experimental position within a water-jacketed $CO_2$ incubator containing a 100% humidified atmosphere of 5 percent $CO_2$ in air at 40° C. Subsequent culture consisted of seven days in the incubator, with fresh medium ever other day.

The dishes containing the left femurs were placed between 15 cm diameter Helmholtz-aiding coils according to the method of the present invention. The non-zero average value of the B field strength was set at 20.9 microTesla. A Beckman FG-2 function generator supplied an 80 Hz ac sine wave along the coil axis, whose amplitude was set at 30 microTesla, peak-to-peak. The frequency of the signal was checked with a Beckman UC-10 frequency counter calibrated against an NBS-referrable source. The amplitude of the ac and static magnetic fields was checked with a single-axis fluxgate magnetometer (Schonstedt Instruments Model 2200-DS) calibrated against NBS standard. AC amplitude was read by feeding the analogue output from the magnetometer to a Tektronix 204A oscilloscope which had also been calibrated against NBS-referrable voltage standards. The magnetic fields were passed through the femurs horizontally.

For the simultaneous treatment, with B set at 20.9 microTesla and the ac frequency ($f_{cs}$) set at 80 Hz, calculation will readily verify that these conditions represent a frequency within 5 percent of the $f_{ch}$ values for $CA^{++}$ where X is 5 and $Mg^{++}$ where X is 3. Independently, these $f_{ch}$ values had been shown previously to be effective for stimulating diatom movement. By using this combination, a concurrent stimulation for both ions could be achieved.

The control cultures were maintained in the same chamber as the experimentals, but shielded from the magnetic fields. The ac magnetic field strength to which the control femurs were subjected was at least two orders of magnitude less than the experimentals (not greater than 0.3 microTesla, peak-to-peak). The ambient 60 Hz magnetic field in the chambers was less than 0.1 microTesla.

At the end of the experiment, the medium was removed from each well of the dishes, and was replaced with an equal amount of Millonig's Neutral Buffered Formalin. After 24 hours to allow for fixation and shrinkage, the femurs were removed gently from the lens paper and the length and central diaphyseal diameters were measured with a pair of metric vernier calipers. The measurement were made and recorded in a blind manner. The femurs were then returned to the wells, but were separated by a small paper divider to keep them separate and identifiable. They were then decalcified and embedded through alcohols and benzene into 54° Paraplast, then cut longitudinally at 8 microns and stained with Mayer's Haematoxylin and Eosin.

The sections were examined under a light microscope (Olympus CH-2) and measurements of the diaphyseal collar length and thickness were made with an ocular micrometer. An assessment of the degree of maturation was also made, together with notes on the histological appearance of the bones. Detailed morphometric analysis was not undertaken, since the differences were either so striking that a resort to statistics was deemed unnecessary, except with regard to the measurements of length, diameter, collar length, and collar thickness. For those measurements, a Student's T-test of the paired experimentals and controls was performed. The experiment was performed in duplicate, so that there were 96 bones in the ionic group, 48 experimentals and 48 controls. These numbers gave clear statistic inferences.

The numerical results of all experiments are presented in Table I below:

TABLE I

| Results of Chick Femur Tests | |
|---|---|
| Category of Measurement | Ca/Mg |
| 1. Bone Length (mm) | 8.7* |
| S.D. | 0.8 |
| Controls | 7.8 |
| S.D. | 0.7 |
| 2. Bone Diameter (mm) | 1.03* |
| S.D. | 0.12 |
| Controls | 0.70 |
| S.D. | 0.08 |
| 3. Length/Diameter | 9.1* |
| S.D. | 0.7 |
| Controls | 11.1 |
| S.D. | 1.03 |
| 4. Collar Length (mm) | 2.31* |
| S.D. | 0.53 |
| Controls | 1.16 |
| S.D. | 0.23 |
| 5. Collar Thickness (mm) | 0.045* |
| S.D. | 0.014 |
| Controls | 0.025 |
| S.D. | 0.008 |

*$p < .01$ compared to paired control value

Controls: there was no statistically significant difference between the values for the two runs. Hence, they were pooled.

The histological appearance of the controls did not vary from run to run. The picture they presented was essentially normal. The ends of the bones were composed of relatively condensed and cellular hyaline cartilage. The diaphyseal collar was quite thin, but well-ossified, while the central diaphyseal region had modestly hypertrophied chondrocytes, with a few pyknotic nuclei, but little or no calcification of the cartilage matrix.

Experimental Treatment: When both calcium and magnesium ions were subjected to CR conditions, the results were essentially a combination of those seen previously for calcium and magnesium separately. The bones were significantly (p (0.01) lengthened (+12%) and thickened (+47%), and the diaphyseal collar length (+99%) and thickness (+80%) were also increased (p (0.01). Robustness increased by 22%.

Histologically, the bones were, as with calcium ion stimulation, advanced with respect to calcification, the central diaphyseal region showing marked calcification. However, the degree of this effect was slightly less than with calcium stimulation alone. The rest of the bone showed generalized enlargement, as with magnesium ion tuning alone.

EXAMPLE 3

A study of simultaneous multiple ion tuning was performed using fibular ostectomies in skeletally mature rabbits. Twelve skeletally mature (2.5 Kg) New Zealand White rabbits of mixed sex were divided into two groups of six animals each and anaesthetized. After anaesthesia, both legs were shaved laterally and painted with betadyne solution. An incision was made 1 cm caudal to the knee, extending for 2.5 cm. The muscles of the anterior and peroneal compartments were separated to expose the fibula. The periosteum was split and reflected from the bone. On the right, the periosteum was allowed to return to place. These bones served as the sham operations. On the left, a 1 cm piece of the fibula was removed from the bone, beginning approximately 1 cm cranial to the union of fibula and tibia. The periosteum was allowed to return. These bones served as the operated series. The wounds of both sides were then closed in layers, ending with stainless steel sutures. The animals were then returned to their cages for recovery.

Six animals were placed in cages which lay between pairs of Helmholtz-aiding coils., according to the method of the present invention. They were stimulated for ½ hour per day. The six animals then exposed to a fluctuating magnetic field tuned to calcium and magnesium simultaneously, using the method of the present invention. The non-zero average value of the (B) field was 40 $\mu$ Tesla, 30 microTesla peak-to-peak, and the frequency ($f_{cs}$) was 153 Hz. This set of conditions, as may be readily seen, provides a value $f_{cs}$ which is within 5 percent of $f_{ch}$ for calcium where X is 5 and for magnesium where X is 3. The other six animals received no magnetic field stimulation and served as controls.

After one month of stimulation, the rabbits were removed from the cages and necrotized by $CO_2$ inhalation. The legs were disarticulated and removed. A-P radiographs were taken of each leg, and the muscle tissue was then stripped from the bones. The diameters of fabellae and callus were measured from the radiographs with a digital micrometer. The fibulas were removed and clamped into a cantilever bending testing jig. Each femur was then bent in the A-P axis by moving the bone with a micrometer screw against the tip of a force transducer positioned 1.5 cm above the tip of the clamp jaws. This length of bone included the ostectomy site. The bones were bent 1 mm, and the force required to produce the bending was recorded by an oscillograph connected to a computer, which produced on-screen graphs of force vs. deflection. The F-D ratios of operated vs. sham-operated sides were compared.

The results of the tests are presented graphically in Table A.

TABLE A

| | OSTECTOMY RESULTS | | |
|---|---|---|---|
| Condition | Fabellar Diam. (mm) | Callus Diam. (mm) | F-D Ratio |
| Control | 2.73 +− .39 | 2.81 +− .52 | .57 +− .26 |
| Ca/Mg 5/3 | 3.77 +− .49# | 3.99 +− .84# | 1.88 +− .74# |

From these results, it can be seen that the application of fields harmonically tuned to cyclotron resonance conditions for calcium and magnesium simultaneously, according to the method of the present invention, produces the growth and osteogenetic effects of magnesium with the mineralization effects of calcium.

These examples offer evidence as to the efficacy of both odd multiple harmonic tuning and the utility of simultaneous turning to more than one ion. It is to be understood that other simultaneous tunings are possible, using harmonic degeneracies, and that the present examples are not meant to be exclusive of other applications or pairings. Any pairing where a degeneracy can be found at complementary odd harmonics is contemplated by the present invention.

What is claimed is:

1. A method for controlling tissue growth, comprising:
    providing a pair of opposed coils and means for electrically energizing said coils;
    providing a human subject in an ambient magnetic field;
    generating an oscillating applied magnetic field along an axis projecting through a region of a human subject by producing an offset sinusoidal signal from said electrical energy source and energizing said coils with said offset sinusoidal signal, said applied magnetic field combining with a component of said ambient field along said axis to form an oscillating magnetic field along said axis having a non-zero net average value;
    creating and maintaining a ratio between the frequency of said oscillating magnetic field and said net non-zero average value of said magnetic field by selecting a frequency of said oscillating magnetic field which is equal to $XBq/2\pi m$, where B is said net non-zero average value, q is the charge of an ion in Coulombs, m is the mass of said ion in kilograms, X is an odd integer greater than 1 and frequency is in Hertz.

* * * * *